United States Patent [19]
Komiya et al.

[11] Patent Number: 5,929,290
[45] Date of Patent: Jul. 27, 1999

[54] COMPOUND AND SURFACTANT

[75] Inventors: Kaoru Komiya; Hiromasa Kawamata; Shohei Umezawa, all of Tokyo, Japan

[73] Assignee: Asahi Denka Kogyo K. K., Tokyo, Japan

[21] Appl. No.: 08/913,856

[22] PCT Filed: Jan. 28, 1997

[86] PCT No.: PCT/JP97/00186

§ 371 Date: Sep. 29, 1997

§ 102(e) Date: Sep. 29, 1997

[87] PCT Pub. No.: WO97/28111

PCT Pub. Date: Aug. 7, 1997

[30] Foreign Application Priority Data

Jan. 30, 1996 [JP] Japan ........................ 8-14441
Feb. 9, 1996 [JP] Japan ........................ 8-23908

[51] Int. Cl.⁶ .................................................. C07C 43/18
[52] U.S. Cl. .......................... 568/616; 510/422; 524/460; 526/209
[58] Field of Search ............................. 568/616; 510/422, 510/130; 524/460, 458; 526/209, 210

[56] References Cited

FOREIGN PATENT DOCUMENTS 06032904  2/1994  Japan .
06234858  8/1994  Japan .

*Primary Examiner*—Gary Geist
*Assistant Examiner*—Sreeni Padmanabhan
*Attorney, Agent, or Firm*—Oblon, Spivak, McClelland, Maier & Neustadt, P.C.

[57] ABSTRACT

A novel polymerizable surfactant represented by the general formula (1):

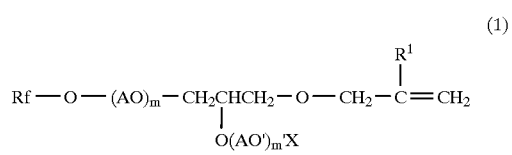

(wherein, $R^1$ represents a hydrogen atom or a methyl group, Rf represents a hydrocarbon group in which one or more hydrogen atoms are replaced by a fluorine atom or atoms, or an acyl group in which one or more hydrogen atoms are replaced by a fluorine atom or atoms, AO and AO' represent a group selected from an oxyalkylene group having 2–4 carbon atoms or a styrene oxide residue, m and m' are 0 or a number between 1 and 1,000, X represents a hydrogen atom or a hydrophilic group).

15 Claims, No Drawings

COMPOUND AND SURFACTANT

This is the U.S. National Stage Application of PCT/JP97/00186 filed Jan. 28, 1997 now WO97/28111 published Aug. 7, 1997.

TECHNICAL FIELD

The present invention relates to a novel compound, and more particularly, the invention relates to a novel polymerizable surfactant. The invention also relates to a specific use of said polymerizable surfactant.

BACKGROUND ART

Surfactants have a wide range of properties including emulsifying properties, dispersing properties, detergent properties, wetting properties and foaming properties. These properties have allowed the surfactants to be used in various fields including paper, rubber, plastics, metals, paints, pigments and civil engineering, in addition to the field of fibers. In particular, moves toward more high performance end products containing surfactants have recently become more active and along with this activity the shortcoming of surfactants are also being pointed out.

For example, surfactants are an indispensable ingredient for producing paints, printing inks, adhesives and the like or for stabilizing these products or improving their workability. However, conventional surfactants are not necessary when products containing such surfactants are actually used in the coating, printing or adhesive process, etc. Rather, in this case the presence of the surfactant most often deteriorates properties such as the water or oil resistance of the paint coat, printed surface, adhesive coat and the like.

In the case wherein a polymer is produced by emulsion polymerization, anionic surfactants such as an alkylsulfate, alkylbenzenesulfate, and polyoxyethylene alkyl ether sulfate and nonionic surfactants such as a polyoxyethylene alkyl ether, polyoxyethylene fatty ester, and pluronic type surfactants have been conventionally used as the emulsifying agent for the emulsion polymerization. It is known that the emulsifying agent for emulsion polymerization is not only involved in initiation of the polymerization reaction or generation reaction, but also relates to the mechanical stability, chemical stability, freezing stability and storing stability of the emulsion produced. Moreover, the emulsifying agent also has a large affect on physical properties of the emulsion such as particle size, viscosity and foaming property, as well as physical properties or film properties, of film made from the emulsion such as water resistance, weather resistance, adhesive property and heat resistance.

However, it has been pointed out that emulsions obtained by emulsion polymerization using the above-mentioned ordinary emulsifying agents generate a lot of bubbles which are attributable to the emulsifying agents. Also, when a film is produced from the emulsion, the free emulsifying agent is left in the film and degrades the film properties such as adhesive property, water resistance, weather resistance and heat resistance.

Conventionally, a dispersing agent in which vinyl chloride type monomers are dispersed in an aqueous medium in the presence of a dispersion stabilizer, has been widely used in suspension polymerization for industrial product film of vinyl resins; and polymerization is carried out using an oil soluble catalyst. The factors controlling the quality of such resins include: polymerization rate, water/monomer ratio, polymerization temperature, type and amount of the catalyst, type of polymerization phase, and stirring speed or type and amount of dispersion stabilizer. Among these, the type of dispersion stabilizer used is known to have a very significant influence.

Examples of a dispersing agent for conventional suspension polymerization of vinyl resins include cellulose derivatives such as methyl cellulose, hydroxypropyl methyl cellulose, carboxy methyl cellulose, and water soluble polymers such as gelatin and polyvinyl alcohol. However, such dispersing agents remain in the free state in the vinyl resin obtained after polymerization and degrade physical properties such as water resistance, weather resistance and durability of the vinyl resin.

As for vinyl resin reforming agents, an example of a vinyl polymer reforming agent is given in Japanese Patent Laid-open NO. 1-174511, but such a reforming agent has not been able to provide a uniform copolymer due to its low compatibility with monomers. An attempt to improve the compatibility of the reforming agent is disclosed in Japanese Patent Laid-Open NO. 1-174512, but compatibility has not yet been improved to a satisfactory level, and the reforming effect on the polymer remained insufficient as well.

Generally speaking, polyester fibers have higher hydrophobic properties and lower hydrophilic properties than natural fibers. This fact has caused the following defects, where polyester fibers are uncomfortable to wear, accumulate static electricity, absorb dust in the air, are difficult to remove oil stains from blacken due to recontamination during washing, etc. There have been various experiments made in the past to get rid of these defects.

Soil resistant finish processes for polyester fibers include a method in which a water soluble polyester resin having increased affinity to polyester fibers is adsorbed (Japanese Patent Publication No. 53-47437), and a method in which the adsorption is carried out using a pad-steam process utilizing a steamer (Japanese Patent Publication No. 51-2559). Methods in which stain proof properties and hydrophilic properties are imparted by graft polymerization of the stain-proofing agent on polyester have been also disclosed in Japanese Patent Laid-open NO. 4-214467 and Japanese Patent Laid-open NO. 4-214466, etc. However, none of the above mentioned methods are fully satisfactory from the view point of performance, and polyester fibers having sufficient stainproof properties have not yet been obtained.

Generally, the conditions for emulsion polymerization and suspension polymerization are diverse. The conditions vary and depend on the type and molecular weight of the polymer to be polymerized, as well as on the manufacturing equipment condition, cost and use of the polymer produced, etc. Thus, an emulsifying agent and dispersing agent that are appropriate for each condition are required. The same can be said about the resin reforming agents and stain resistant finish for polyester fibers.

The performance of the surfactant is mainly decided by the balance between the hydrophilic group and the hydrophobic group. However, sometimes conventional polymerizable surfactants fail to show sufficient hydrophobic properties and thus has been a demand in the industry for a polymerizable surfactant having a novel hydrophobic group.

DISCLOSURE OF THE INVENTION

The inventors have intensively studied and developed a novel compound having a hydrocarbon group containing a fluorine atom as a hydrophobic group, and a use thereof, and thus completed the present invention. Therefore, according to the present invention there is provided a compound represented by the general formula (1):

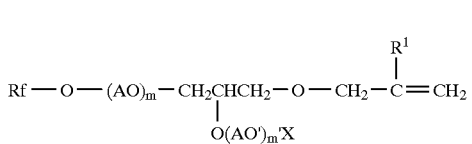

(wherein, $R^1$ represents a hydrogen atom or a methyl group, Rf represents a hydrocarbon group in which one or more hydrogen atoms are replaced by a fluorine atom or atoms, or an acyl group in which one or more hydrogen atoms are replaced by a fluorine atom or atoms, AO and AO' represent a group selected from an oxyalkylene group having 2–4 carbon atoms or a styrene oxide residue, m and m' are 0 or a number between 1 and 1,000, X represents a hydrogen atom or a hydrophilic group), and a surfactant comprising said compound.

BEST MODE FOR CARRYING OUT THE INVENTION

In the above-mentioned general formula (1), $R^1$ represents a hydrogen atom or a methyl group. Rf represents a hydrocarbon group in which one or more hydrogen atoms are replaced by a fluorine atom or atoms, or an acyl group in which one or more hydrogen atoms are replaced by a fluorine atom or atoms. Examples of the hydrocarbon group include fluoroalkyl, fluoroalkenyl, fluoroaryl, fluorocycloalkyl, fluorocycloalkenyl and the like.

Examples of the fluoroalkyl group include a perfluoroalkyl group represented by $C_nF_{2n+1}$ such as perfluoromethyl, perfluoroethyl, perfluoropropyl, perfluoroisopropyl, perfluorobutyl, perfluoroisobutyl, perfluorotertiary butyl, perfluoropentyl, perfluoroisopentyl, perfluoroneopentyl, perfluorotertiary pentyl, perfluorohexyl, perfluoroheptyl, perfluorooctyl, perfluoro 2-ethylhexyl, perfluorononyl, perfluorodecyl, perfluoroundecyl, perfluorododecyl, perfluorotridecyl, perfluoroisotridecyl, perfluorotetradecyl, perfluorohexadecyl, perfluorooctadecyl, perfluoroicosyl, perfluorodocosyl, perfluorotetracosyl, perfluorotriacontyl, perfluoro-2-octyl-dodecyl, perfluoro-2-dodecyl-hexadecyl, and perfluoro 2-tetradecyl-octadecyl, a fluoroalkyl group represented by $C_nF_{2n-1}H_2$ or $F(CF_2)_{n-1}CH_2$— such as trifluoroethyl, pentafluoropropyl, heptafluorobutyl, nonafluoropentyl, undecafluorohexyl, tridecafluoroheptyl, pentadecafluorooctyl, heptadecafluorononyl, nonadecafluorodecyl, henicosafluoroundecyl, tricosafluorododecyl, pentacosafluorotridecyl, heptacosafluorotetradecyl, nonacosafluoropentadecyl, a fluoroalkyl group represented by $C_nF_{2n-2}H_3$ or $H(CF_2)_{n-1}CH_2$— such as difluoroethyl, tetrafluoropropyl, hexafluorobutyl, octafluoropentyl, decafluorohexyl, dodecafluoroheptyl, tetradecafluorooctyl, hexadecafluorononyl, octadecafluorodecyl, icosafluoroundecyl, docosafluorododecyl, tetracosafluorotridecyl, hexacosafluorotetradecyl, octacosafluoropentadecyl, and triacontafluorohexadecyl, and a fluoroalkyl group represented by $C_nF_{2n-3}H_4$ or $F(CF_2)_{n-2}CH_2CH_2$— such as monofluoroethyl, trifluoropropyl, pentafluorobutyl, heptafluoropentyl, nonafluorohexyl, undecafluoroheptyl, tridecafluorooctyl, pentadecafluorononyl, heptadecafluorodecyl, nonadecafluoroundecyl, henicosafluorododecyl, tricosafluorotridecyl, pentacosafluorotetradecyl, heptacosafluoropentadecyl, and nonacosafluorohexadecyl, and a fluoroalkyl group represented by $C_nF_{2n-5}H_6$ or $F(CF_2)_{n-3}CH_2CH_2CH_2$— such as monofluoropropyl, trifluorobutyl, pentafluoropentyl, heptafluorohexyl, nonafluoroheptyl, undecafluorooctyl, tridecafluorononyl, pentadecafluorodecyl, heptadecafluoroundecyl, nonadecafluorododecyl, henicosafluorotridecyl, tricosafluorotetradecyl, pentacosafluoropentadecyl, and heptacosafluorohexadecyl, and a fluoroalkyl group represented by $C_nF_{2n-11}H_{12}$ or $F(CF_2)_{n-6}(CH_2)_6$— such as monofluorohexyl, trifluoroheptyl, pentafluorooctyl, heptafluorononyl, nonafluorodecyl, undecafluoroundecyl, tridecafluorododecyl, pentadecafluorotridecyl, heptadecafluorotetradecyl, nonadecafluoropentadecyl, and henicosafluorohexadecyl.

Examples of a fluoroalkenyl group include a perfluoroalkenyl group such as perfluoropropenyl, perfluoroisopropenyl, perfluorobutenyl, perfluoroisobutenyl, perfluoropentenyl, perfluoroisopentenyl, perfluorohexenyl, perfluoroheptenyl, perfluorooctenyl, perfluorononenyl, perfluorodecenyl, perfluoroundecenyl, perfluorododecenyl, perfluorotetradecenyl, perfluorooleyl and a fluoroalkenyl group represented by $C_nF_{2n-5}H_4$ or $F(CF_2)_{n-3}$—CH=CHCH$_2$— such as trifluorobutenyl, pentafluoropentenyl, heptafluorohexenyl, nonafluoroheptenyl, undecafluorooctenyl, tridecafluorononenyl, pentadecafluorodecenyl, heptadecafluoroundecenyl, nonadecafluorododecenyl, and henicosafluorotetradecenyl.

Examples of a fluoroaryl group include a perfluoroaryl group such as perfluorophenyl, perfluorotoluyl, perfluoroxylyl, perfluorocumenyl, perfluoromesityl, perfluorobenzyl, perfluorophenethyl, perfluorostyryl, perfluorocinnamyl, perfluorobenzhydryl, perfluorotorityl, perfluoroethylphenyl, perfluoropropylphenyl, perfluorobutylphenyl, perfluoropentylphenyl, perfluorohexylphenyl, perfluoroheptylphenyl, perfluorooctylphenyl, perfluorononylphenyl, perfluorodecylphenyl, perfluoroundecylphenyl, perfluorododecylphenyl, perfluorostyrenated phenyl, perfluoro p-cumylphenyl, perfluorophenylphenyl, and perfluorobenzylphenyl, and monofluorophenyl, difluorophenyl, trifluorophenyl, tetrafluorophenyl, monofluorotoluyl, (perfluoromethyl)phenyl, (trifluoromethyl)monofluorophenyl, (perfluoroethyl)phenyl, (perfluoropropyl)phenyl, (perfluorobutyl)phenyl, (perfluoropentyl)phenyl, (perfluorohexyl)phenyl, (perfluoroheptyl)phenyl, (perfluorooctyl)phenyl, (perfluorononyl)phenyl, (perfluorodecyl)phenyl, (perfluoroundecyl)phenyl, and (perfluorododecyl)phenyl and the like.

Examples of a fluorocycloalkyl group and fluorocycloalkenyl group include perfluorocyclopentyl, perfluorocyclohexyl, perfluorocycloheptyl, perfluoromethylcyclopentyl, perfluoromethylcyclohexayl, perfluoromethylcycloheptyl, perfluorocyclopentenyl, perfluorocyclohexenyl, perfluorocycloheptenyl, perfluoromethylcyclopentenyl, perfluoromethylcyclohexenyl, perfluoromethylcycloheptenyl and the like.

Examples of a fluoroacyl group include a group in which a carbonyl group is bonded to the bonding end of the above-mentioned fluorocarbon group. Examples thereof include a perfluoroacyl group such as perfluoroacetyl, perfluoropropionyl, perfluorobutyryl, perfluoroisobutyryl, perfluorovaleryl, perfluoroisovaleryl, perfluoropivalyl, perfluorododecanoyl, perfluorotetradecanoyl, perfluorohexadecanoyl, perfluorooctadecanoyl, perfluoroacryloyl, perfluoropropioloyl, perfluoromethacroyl, perfluorocrotonoyl, perfluorooleyloyl, perfluorobenzoyl, perfluorophthaloyl, and perfluorosuccinyl, and monofluoroacetyl, difluoroacetyl, tetrafluoropropionyl, hexafluorobutyryl, octafluorovaleryl, docosafluorododecanoyl, octacosafluorotetradecanoyl, and triacontafluorohexadecanoyl.

Among the above-mentioned hydrocarbon groups in which one or more hydrogen atoms are replaced by a fluorine atom or atoms, or acyl groups in which one or more hydrogen atoms are replaced by a fluorine atom or atoms, $F(CF_2)_{n-1}CH_2$—, $H(CF_2)_{n-1}CH_2$— or a perfluoroacyl group are preferred.

AO and AO' in the general formula (1) represent an oxyalkylene group such as oxyethylene, oxypropylene, and oxybutylene or styrene oxide residue. An AO and AO' moiety can be obtained by addition polymerization of an alkylene oxide such as ethylene oxide, propylene oxide, butylene oxide and epichlorohydrin or styrene oxide; AO and AO' are decided by the added alkylene oxide and the like. The alkylene oxide and the like to be added can be a homopolymer, a random copolymer, block copolymer or random/block copolymer of two or more types. The method of addition can be a known method. AO and AO' are preferably an oxyethylene group; it is preferable that at least one of them is an oxyethylene group when two or more oxyalkylene groups or styrene oxide residue are used so that sufficient hydrophilic properties can be obtained. The polymerization degree m and m' are numbers between 1 and 1,000 and m is preferably 0, m' is preferably 1–500, more preferably 5–100.

In the general formula (1), X represents a hydrogen atom (hydroxyl group) or a hydrophilic group. Examples of the hydrophilic group include: —$SO_3M$, —$R^2$—COOM, —$PO_3M_2$, —$PO_3MH$ or —CO—$R^3$—COOM and the like.

In the above-mentioned formula representing the hydrophilic groups, M represents a hydrogen atom, an alkali metal atom such as lithium, sodium, and potassium, an alkaline earth metal atom such as magnesium, and calcium (provided that the alkaline earth metal atom is usually divalent, thus ½), ammonium of ammonia, ammonium of an alkylamine such as monomethylamine and dipropylamine, or ammonium of an alkanolamine such as monoethanolamine, diethanolamine, and triethanolamine.

$R^2$ represents an alkylene group such as methylene, ethylene, propylene, butylene, pentene, pentamethylene, and hexamethylene. Among these, an alkylene group having 1–3 carbon atoms such as methylene, ethylene, propylene are preferable from the view point of availability.

$R^3$ represents a residue of a dibasic acid or an anhydride thereof. Examples of the dibasic acid include saturated aliphatic dicarboxylic acids such as oxalic acid, malonic acid, succinic acid, glutaric acid, adipic acid, pimelic acid, suberic acid, azelaic acid, sebacic acid, undecanedioic acid, dodecanedioic acid., tridecanedioic acid, and tetradecanedioic acid, saturated alicyclic dicarboxylic acids such as cyclopentanedicarboxylic acid, hexahydrophthalic acid, and methylhexahydrophthalic acid, aromatic dicarboxylic acids such as phthalic acid, isophthalic acid, terephthalic acid, tolylene dicarboxylic acid, and xylylene dicarboxylic acid, unsaturated aliphatic dicarboxylic acids such as maleic acid, fumaric acid, itaconic acid, citraconic acid, and mesaconic acid, and unsaturated alicyclic dicarboxylic acids such as tetrahydrophthalic acid, methyltetrahydrophthalic acid, nadic acid (endo methylene tetra hydro phthalic acid), methyl nadic acid, methyl butenyl tetrahydrophthalic acid, and methyl pentenyl tetrahydrophthalic acid. These can also be used in the form of an anhydride thereof.

The compound of the present invention can be used as a surfactant and in particular, it can be used as a surfactant having reactivity with a radical polymerization system such as a vinyl group. Accordingly, it can be used as an emulsifying agent for emulsion polymerization, a dispersing agent for suspension polymerization, a resin reforming agent (for improving water repellency, controlling hydrophilic properties, and improving compatibility, antistatic properties, anti-fog properties, water resistance, adhesion, dye-affinity, film forming properties, weather resistance, blocking resistance, and the like), a fiber processing aid, anti-droplet agent, fiber stain-proofing agent, and the like. It can be also used as a raw material for producing a copolymer type surfactant (examples are shown in Japanese Patent Application No. 8-271026 and the like).

When the compound of the present invention is used as the emulsifying agent for emulsion polymerization, it can be used in an arbitrary amount within the range for normal use of a conventionally known emulsifying agent for emulsion polymerization, and in general it is preferably 0.1–20% by weight, more preferably 0.2–10% by weight based on the raw material monomers. The emulsifying agent for emulsion polymerization of the present invention can be used together with another polymerizable or nonpolymerizable emulsifying agent. The monomers to be polymerized by emulsion polymerization are not particularly limited. This emulsifying agent can be preferably used for acrylate type emulsion, styrene type emulsion, vinyl acetate type emulsion, SBR (styrene/butadiene) emulsion, ABS (acrylonitrile/butadiene/styrene) emulsion, BR (butadiene) emulsion, IR (isoprene) emulsion, NBR (acrylonitrile/butadiene) emulsion, and the like.

Examples of the acrylate type emulsion include: (meth) acrylic acid (ester)/(meth)acrylic acid (ester), (meth)acrylic acid (ester)/styrene, (meth)acrylic acid (ester)/vinyl acetate, (meth)acrylic acid (ester)/acrylonitrile, (meth)acrylic acid (ester)/butadiene, (meth)acrylic acid (ester)/vinylidene chloride, (meth)acrylic acid (ester)/allylamine, (meth) acrylic acid (ester)/vinyl pyridine, (meth)acrylic acid (ester)/ alkylol amide, (meth)acrylic acid (ester)/N,N-dimethylaminoethyl ester, (meth)acrylic acid (ester)/N,N-diethylaminoethyl vinyl ether, and the like.

Examples of the styrene type emulsion include: styrene alone or styrene/acrylonitrile, styrene/butadiene, styrene/ fumarnitrile, styrene/mallein nitrile, styrene/cyanoacrylic ester, styrene/phenyl vinyl acetate, styrene/chloromethyl styrene, styrene/dichlorostyrene, styrene/vinyl carbazole, styrene/N,N-diphenyl acrylamide, styrene/methyl styrene, acrylonitrile/butadiene/styrene, styrene/acrylonitrile/methyl styrene, styrene/acrylonitrile/vinyl carbazole, styrene/ maleic acid, and the like.

Examples of the vinyl acetate type emulsion include: vinyl acetate alone and vinyl acetate/styrene, vinyl acetate/ vinyl chloride, vinyl acetate/acrylonitrile, vinyl acetate/ maleic acid (ester), vinyl acetate/fumaric acid (ester), vinyl acetate/ethylene, vinyl acetate/propylene, vinyl acetate/ isobutylene, vinyl acetate/vinylidene chloride, vinyl acetate/ cyclopentadiene, vinyl acetate/crotonic acid, vinyl acetate/ acrolein, vinyl acetate/alkyl vinyl ether and the like.

When the surfactant of the present invention is used as a dispersing agent for suspension polymerization, it can be used in an arbitrary amount within the range for a normal use of the conventionally known dispersing agent for suspension polymerization, and in general, it is preferably 0.1–20% by weight, more preferably 0.2–10% by weight based on the raw material monomers. The dispersing agent of the suspension polymerization of the present invention can be used together with another reactive or nonreactive dispersing agent, such as polyvinyl alcohol. The monomers to be polymerized by suspension polymerization are not particularly limited and the above-mentioned monomers having polymerizing carbon-carbon double bond can be used for homopolymerization and copolymerization, however, olefin halide type and vinyl acetate type monomers are preferred.

Examples of olefin halide type monomers to be polymerized include vinyl chloride, vinylidene chloride, vinyl chloride/maleic acid (ester), vinyl chloride/fumaric acid (ester), vinyl chloride/vinyl acetate, vinyl chloride/vinylidene chloride, vinylidene chloride/vinyl acetate, vinylidene chloride/vinyl benzoate, and the like.

The same holds true for the polymerization of vinyl acetate type monomers.

As the surfactant of the present invention contains a fluorine atom, it can be used as an emulsifying agent for emulsion polymerization or a dispersing agent for suspension polymerization of fluorinated olefins. Examples of the fluorinated olefin include: vinyl fluoride, vinylidene fluoride, chlorofluoroethylene, chlorodifluoroethylene, dichlorofluoroethylene, dichlorodifluoroethylene, trifluoroethylene, chlorotrifluoroethylene, tetrafluoroethylene, trifluoeopropylene, pentafluoropropylene, hexafluoropropylene, and the like.

When the surfactant of the present invention is used as an emulsifying agent for emulsion polymerization or a dispersing agent for suspension polymerization, the various problems caused by conventional nonreactive emulsifying agents, such as: foaming of the emulsion or suspension, reduced physical properties of the polymer obtained from the emulsion or suspension (including water resistance, weather resistance, adhesion, and the like), waste water load and environmental disruption (caused because the waste water from the production process contains the emulsifying agent), can be solved since the surfactant of the present invention has a polymerizable double bond. As the waste water resulting from the precipitation process does not contain the emulsifying agent or dispersing agent, it has the merit of causing no waste water load or environmental disruption. This point is a particularly remarkable achievement for the production of ABS resin.

When the surfactant of the present invention is used as a resin reforming agent, physical properties of the resin are reformed; i.e. the hydrophilic property is controlled, compatibility with a polymer and a monomer is improved, antistatic properties are improved, anti-fog properties are improved, water resistance is improved, adhesion is improved, dye-affinity is improved, film forming properties are improved, weather resistance is improved, and blocking resistance is improved. The resins to be reformed are not particularly limited and all of the resins produced by polymerization of the above-mentioned monomers can be used. Such resin reforming agents can be used for polyester resins, polyamide resins, polyimide resins, polyaryl ether resins, epoxy resins and urethane resins, and the like. Polyolefin halides derived from monomers such as vinyl chloride and vinylidene chloride, and poly α-olefins derived from monomers such as ethylene and propylene are preferred. The resin reforming agent of the present invention can be added to the resin by coating it on the resin's surface or by incorporating it in the resin during the processing of the resin. The resin reforming agent of the present invention can be polymerized as one of the monomer components with other monomers when the resin is produced so as to be incorporated in the molecule of the resin to give permanent reforming activities such as permanent antistatic properties.

The resin reforming agent of the present invention shows excellent compatibility with monomers by the use of a compound having an ether chain in the structure. When the resin reforming agent contains AO and AO', the hydrophilic property can be easily controlled by selecting, if necessary, the polymerization degree of the oxyalkylene group (m and m') and the type of oxyalkylene group according to the purpose of the reformation and compatibility with the monomers. Therefore, the resin reforming agent of the present invention can improve both the compatibility with monomers and the reformation of the polymer at the same time. By the use of the resin reforming agent of the present invention, it is possible to impart permanent antistatic properties and anti-fog properties to the resin used.

The amount of resin reforming agent used according to the present invention can be changed depending on the type of the monomers, purpose of the reformation, required performance, and the like, but is preferably used in an amount of 0.1–80% by weight based on the monomers. In particular, when a water soluble resin having insufficient hydrophilic properties is desired to be converted into a polymer having high hydrophilic properties, the resin reforming agent can be preferably used in an amount of 1–80% by weight based on the monomers. For other uses, such as improving water resistance, adhesion, anti-static properties, anti-fog properties, dye-affinity, film forming properties, weather resistance and blocking resistance, or for imparting compatibilizing properties to a polymer for producing a polymer alloy, the resin reforming agent is preferably used in an amount of 0.1–60% by weight based on the monomers.

When the resin reforming agent of the present invention is used, a crosslinking divinyl compound and the like such as divinyl benzene, ethylene glycol dimethacrylate, and methylenebisacrylamide can be used in an arbitrary amount within the range of ordinary use to improve the physical properties of the resin. Furthermore, when the resin reforming agent is used as an emulsifying agent for emulsion polymerization, a dispersing agent for suspension polymerization, a resin reforming agent, etc., the resin polymer can be crosslinked by the presence of a metal oxidizing agent.

When the surfactant of the present invention is used for a soil resistant finish for polyester fibers, the stainproof property can be imparted by graft polymerization of the compound on the polyester fiber. The method of graft polymerization is not particularly limited and a known process can be used. For example, a method utilizing exposure to ionizing radiation, a method utilizing ionic discharge, a method utilizing thermal oxidation or ozone oxidation, a method utilizing a radical polymerization initiating catalyst, or graft polymerization method utilizing no catalyst can be used. If necessary, the stain-proofing agent of the present invention can be mixed with a perfume, a fluorescent agent, or any other components. The polyester fibers in which the stain-proofing agent of the present invention is incorporated by graft polymerization shows much improved stainproof properties and resistance to recontamination when compared to non-treated polyester fiber, and also shows antistatic properties, etc.

The production process of the compound of the present invention is not particularly limited; for example, a compound of the present invention wherein X is a hydrogen atom can be produced by adding an alkylene oxide, etc., to the reaction product resulting from the reaction between (meth)allyl glycidyl ether, and an alcohol or a phenol or carboxylic acid in which one or more hydrogen atoms are replaced with a fluorine atom or atoms. In order to confirm the completion of the reaction between the (meth)allyl glycidyl ether, and an alcohol or a phenol or carboxylic acid in which one or more hydrogen atoms are replaced with a fluorine atom or atoms, IR absorption or measurement of the epoxy equivalent can, for example, be used. Or, if necessary, a catalyst can be used. The usable catalysts are not particularly limited as far as they can be used for a ring-opening reaction of an epoxy, and examples thereof include: a tertiary amine, quaternary ammonium salt, boron trifluoride or an ether complex salt thereof, aluminium chloride, barium oxide, sodium hydroxide, potassium hydroxide, and the like.

The reaction conditions for the reaction with an alkylene oxide, etc. are not particularly limited, but normally: the temperature is between room temperature and 150° C., the pressure is 0.1–10 kg/cm$^2$G, and if necessary, sodium hydroxide, potassium hydroxide, boron trifluoride, and the like can be used as a catalyst. For producing a compound in which X is a hydrophilic group, the hydrophilic group is introduced into the compound obtained by the above-mentioned reaction.

Among the formulas representing the hydrophilic group, the group represented by —SO$_3$M is introduced by sulfation using a hydrophilization agent such as sulfamic acid, sulfuric acid, sulfuric anhydride, fuming sulfuric acid, and chlorosulphonic acid. The reaction conditions for sulfation are not particularly limited, however, the temperature is usually between room temperature and 150° C., the pressure is between normal pressure and about 5 kg/cm$^2$, and the reaction time is between 1 and about 10 hours.

Among the formulas representing the hydrophilic group, the group represented by —PO$_3$M$_2$ or —PO$_3$MH is introduced by phosphorylation using a hydrophilization agent such as diphosphorus pentaoxide, polyphosphoric acid, and phosphorus oxychloride. In the phosphorylation, a monoester type compound and a diester type compound are obtained in mixture and they can be separated for use, or if the separation is difficult, they can be used in the form of a mixture. The reaction conditions for phosphorylation are not particularly limited, however, the temperature is normally. between room temperature and 150° C., the pressure is normal pressure, and the reaction time is between 1 and about 10 hours.

Among the formulas representing the hydrophilic group, the group represented by —R$^2$—COOM is introduced by carboxylation using a hydrophilization agent such as chloroacetic acid (corresponding to the case wherein R$^2$ is methyl), chloropropionic acid (corresponding to the case wherein R$^2$ is ethyl), or a salt thereof. The reaction conditions for carboxylation are not particularly limited, however, the temperature is normally between room temperature and 150° C., the pressure is between normal pressure and around 5 kg/cm$^2$, and the reaction time is between 1 and about 10 hours. If necessary, an alkali such as sodium hydroxide and potassium hydroxide can be used as a catalyst.

Among the formulas representing the hydrophilic group, the group represented by —CO—R$^3$—COOM is introduced by carrying out conversion into a dibasic acid, using a hydrophilization agent such as the above-mentioned dibasic acid or an anhydride thereof. For example, maleic acid (corresponding to the case wherein R$^3$ is CH=CH group), phthalic acid (corresponding to the case wherein R$^3$ is phenyl), and a salt thereof or an anhydride thereof can be used. The reaction conditions for this conversion are not particularly limited, however, the temperature is normally between room temperature and 150° C., the pressure is normal pressure, and the reaction time is between 1 and about 10 hours. If necessary, an alkali such as sodium hydroxide and potassium hydroxide can be used as a catalyst.

When hydrophilization is carried out, it can be followed by neutralization using an alkali such as sodium hydroxide, potassium hydroxide, and/or ammonia, an alkyl amine or alkanol amine such as monoethanol amine and diethanol amine.

EXAMPLES

To further illustrate the present invention, the following Examples are presented. In the following Examples etc., Percent and parts are based on weight, unless otherwise stated.

Production Example 1

A 1 L four-neck glass flask was charged with 500 g of C$_6$F$_{13}$OH, and 5 g of sodium hydroxide as a catalyst and subjected to dehydration under a reduced pressure of 10 mmHg or less at 80±5° C. for 1 hour. Then nitrogen was added to return the pressure to a normal pressure and 175 g of allyl glycidyl ether was added thereto dropwise using a dropping funnel. After the dropping, reaction was carried out at 80±5° C. for 5 hours to obtain a compound of the present invention (1-a).

A pressure reactor was charged with 1 mole of the compound produced in the present invention (1-a) and 30 moles of ethylene oxide, then reaction was carried out at a reaction temperature of 80° C. and a starting pressure of 4 kg/cm$^2$ for 15 hours to obtain a compound of the present invention (1-b) in which 30 moles of ethylene oxide were added.

Production Example 2

A reaction analogous to that of Production Example 1 was carried out except that C$_{12}$F$_{25}$OH was used instead of C$_6$F$_{13}$OH and triethylamine was used as the catalyst for adding 60 moles of ethylene oxide to give a compound of the present invention (2).

Production Example 3

Reaction analogous to that of Production Example 1 was carried out except that C$_{18}$F$_{37}$OH was used instead of C$_6$F$_{13}$OH and methallyl glycidyl ether was used instead of allyl glycidyl ether in adding 90 moles of ethylene oxide to obtain a compound of the present invention (3).

Production Example 4

200 g of the compound of the present invention (1-a) produced in Production Example 1 was added to a 500 ml four-neck glass flask and cooled to 0–5° C. 115 g of chlorosulfonic acid was added thereto dropwise using a dropping funnel. After dropping, the mixture was stirred at the same temperature for 1 hour and HCl generated was removed by bubbling nitrogen. Then neutralization was carried out using an aqueous solution of sodium hydroxide to obtain a compound of the present invention (4) as a sodium salt.

Production Example 5

The compound of the present invention (1-b) obtained in Production Example 1 was treated with chlorosulfonic acid in a manner similar to that used in Example 4 to obtain a compound of the present invention (5-a) as a sulfuric ester. This was then neutralized with an aqueous solution of potassium hydroxide to give a compound of the present invention (5-b).

Production Example 6

A reaction analogous to that of Production Example 1 was carried out except that $C_{18}F_{37}OH$ was used instead of $C_6F_{13}OH$ and methallyl glycidyl ether was used instead of allyl glycidyl ether for adding 30 moles of ethylene oxide to obtain a compound of the present invention (6-a).

200 g of the compound produced was added to a 500 ml four-neck glass flask and 37 g of phosphorus pentaoxide was added thereto at 40° C., heated to 60° C. and reacted for 2 hours, then the reaction mixture was maintained at 80° C. for 2 hours. Then an aqueous solution of sodium hydroxide was used to carry out neutralization to provide a compound of the present invention (6-b) as a soda salt. Neutralization was also carried out using an aqueous ammonia solution instead of an aqueous solution of sodium hydroxide to give a compound of the present invention (6-c). Neutralization was also carried out using an aqueous solution of magnesium hydroxide instead of an aqueous solution of sodium hydroxide to obtain a compound of the present invention (6-d).

Production Example 7

A reaction analogous to that of Production Example 1 was carried out except that styrene oxide was used instead of ethylene oxide in adding 30, 60 and 90 moles of styrene oxide to obtain compounds of present invention (7-a), (7-b), and (7-c).

Production Example 8

200 g of the compound of the present invention (7-a) produced in Production Example 7 was added to a 500 ml four-neck glass flask and 37 g of phosphorus pentaoxide was added thereto at 40° C., heated to 60° C. and reacted for 2 hours, then the reaction mixture was maintained at 80° C. for 2 hours. Then an aqueous solution of sodium hydroxide was used to carry out neutralization to obtain a compound of the present invention (8) as a soda salt.

Production Example 9

200 g of the compound of the present invention (1-a) produced in Production Example 1 was added to a 500 ml four-neck glass flask and cooled to 60±5° C. 64 g of monochloroacetic acid was added thereto dropwise using a dropping funnel. After the dropping, the mixture was stirred at the same temperature for 1 hour and generated HCl was removed by bubbling nitrogen. Then an aqueous solution of sodium hydroxide was used to carry out neutralization to obtain a compound of the present invention (9-a) as a sodium salt. Neutralization was also carried out using an aqueous solution of potassium hydroxide instead of sodium hydroxide to obtain a compound of the present invention (9-b).

Production Example 10

A procedure analogous to that of Production Example 9 was carried out except that a compound of present invention (1-b) produced in Production Example 1 was used instead of the compound (1-a) to obtain a compound of the present invention (10).

Production Example 11

A 1 L four-neck glass flask was charged with 500 g of $F(CF_2)_3CH_2OH$ and 5 g of a sodium hydroxide catalyst and subjected to dehydration under a reduced pressure of 10 mmHg or less at 80±5° C. for 1 hour. Then nitrogen was added to return the pressure to a normal pressure and 175 g of allyl glycidyl ether was added thereto dropwise using a dropping funnel. After the dropping, reaction was carried out at 80±5° C. for 5 hours. Then a pressure reactor was charged with 1 mole of the resulting reaction product and 10 moles of ethylene oxide and subjected to a reaction at a reaction temperature of 80° C. and a starting pressure of 4 kg/cm$^2$ for 15 hours to give a compound of the present invention (11) in which 10 moles of ethylene oxide were added.

Production Example 12

A compound of the present invention (12) was obtained in a manner similar to that used in Production Example 11 except that $F(CF_2)_6C_2H_4OH$ was used instead of $F(CF_2)_3CH_2OH$ and 20 moles of ethylene oxide were used.

Production Example 13

A compound of the present invention (13) was obtained in a manner similar to that used in Production Example 11 except that $H(CF_2)_8CH_2OH$ was used instead of $F(CF_2)_3CH_2OH$ and 15 moles of ethylene oxide were used.

Production Example 14

A compound of the present invention (14) was obtained in a manner similar to that used in Production Example 11 except that $H(CF_2)_8CH_2OH$ was used instead of $F(CF_2)_3CH_2OH$ and sulphamic acid was used for introducing the hydrophilic group.

Production Example 15

A compound of the present invention (15) was obtained in a manner similar to that used in Production Example 11 except that $H(CF_2)_6CH_2OH$ was used instead of $F(CF_2)_3CH_2OH$, maleic anhydride was used for introducing the hydrophilic group, and sodium hydroxide was used for neutralization.

Production Example 16

A compound of the present invention (16) was obtained in a manner similar to that used in Production Example 11 except that $CF_3PhOH$ was used instead of $F(CF_2)_3CH_2OH$, phthalic anhydride was used for introducing the hydrophilic group, and sodium hydroxide was used for neutralization.

Production Example 17

Compounds of the present invention (17-a) and (17-b) were obtained in a manner similar to that used in Production Example 1 except that $C_6F_{13}COOH$ was used instead of $C_6F_{13}OH$.

Production Example 18

A compound of the present invention (18) was obtained in a manner similar to that used in Production Example 2 except that $C_{12}F_{25}COOH$ was used instead of $C_{12}F_{25}OH$.

Production Example 19

A compound of the present invention (19) was obtained in a manner similar to that used in Production Example 3 except that $C_{18}F_{37}COOH$ was used instead of $C_{18}F_{37}OH$.

Production Example 20

A compound of the present invention (20) was obtained in a manner similar to that used in Production Example 4 except that $C_6F_{17}COOH$ was used instead of $C_6F_{17}OH$.

Production Example 21

Compounds of the present invention (21-a) and (21-b) were obtained in a manner similar to that used in Production Example 5 except that $C_6F_{13}COOH$ was used instead of $C_6F_{13}OH$.

Production Example 22

Compounds of the present invention (22-a), (22-b), (22-c) and (22-d) were obtained in a manner similar to that used in Production Example 6 except that $C_{18}F_{37}COOH$ was used instead of $C_{18}F_{37}OH$.

Production Example 23

Compounds of the present invention (23-a), (23-b) and (23-c) were obtained in a manner similar to that used in Production Example 7 except that $C_6F_{13}COOH$ was used instead of $C_6F_{13}OH$.

Production Example 24

A compound of the present invention (24) was obtained in a manner similar to that used in Production Example 8 except that $C_6F_{13}COOH$ was used instead of $C_6F_{13}OH$.

Production Example 25

Compounds of the present invention (25-a) and (25-b) were obtained in a manner similar to that used in Production Example 9 except that $C_6F_{13}COOH$ was used instead of $C_6F_{13}OH$.

Production Example 26

A compound of the present invention (26) was obtained in a manner similar to that used in Production Example 10 except that $C_6F_{13}COOH$ was used instead of $C_6F_{13}OH$.

Production Example 27

A compound of the present invention (27) was obtained in a manner similar to that used in Production Example 15 except that $C_8F_{17}COOH$ was used instead of $H(CF_2)_6CH_2OH$.

| Prod. Ex. | Structure | | |
|---|---|---|---|
| 1 | $C_6F_{13}-R-CH_2CHCH_2OCH_2CH=CH_2$, side chain $O(EO)n-H$ | 1-a: R=O, n = 0<br>1-b: R=O, n = 30 | 17-a: R=COO, n = 0<br>17-b: R=COO, n = 30 |
| 2 | $C_{12}F_{25}-R-CH_2CHCH_2OCH_2CH=CH_2$, side chain $O(EO)_{60}-H$ | 2: R=O<br>18: R=COO | |
| 3 | $C_{18}H_{37}-R-CH_2CHCH_2OCH_2C(CH_3)=CH_2$, side chain $O(EO)_{90}-H$ | 3: R=O<br>19: R=COO | |
| 4 | $C_6F_{13}-R-CH_2CHCH_2OCH_2CH=CH_2$, side chain $OSO_3Na$ | 4: R=O<br>20: R=COO | |
| 5 | $C_6F_{13}-R-CH_2CHCH_2OCH_2CH=CH_2$, side chain $O(EO)_{30}SO_3M$ | 5-a: R=O, M=H<br>5-b: R=O, M=K | 21-a: R=COO, M=H<br>21-b: R=COO, M=K |
| 6 | $C_{18}F_{37}-R-CH_2CHCH_2OCH_2C(CH_3)=CH_2$, side chain $O(EO)_{30}-X$ | 6-a: R=O, X=H<br>6-b: R=O, X=PO_3Na_2<br>6-c: R=O, X=PO_3(NH_4)_2<br>6-d: R=O, X=PO_3Mg | 22-a: R=COO, X=H<br>22-b: R=COO, X=PO_3Na_2<br>22-c: R=COO, X=PO_3(NH_4)_2<br>22-d: R=COO, X=PO_3Mg |
| 7 | $C_6F_{13}-R-CH_2CHCH_2OCH_2CH=CH_2$, side chain $O(SO)n-H$ | 7-a: R=O, n = 30<br>7-b: R=O, n = 60<br>7-c: R=O, n = 90 | 23-a: R=COO, n = 30<br>23-b: R=COO, n = 60<br>23-c: R=COO, n = 90 |
| 8 | $C_6F_{13}-R-CH_2CHCH_2OCH_2CH=CH_2$, side chain $O(SO)_{30}-PO_3Na_2$ | 8: R=O<br>24: R=COO | |
| 9 | $C_6F_{13}-R-CH_2CHCH_2OCH_2CH=CH_2$, side chain $OCH_2COOM$ | 9-a: R=O, M=Na<br>9-b: R=O, M=K | 25-a: R=COO, M=Na<br>25-b: R=COO, M=K |

-continued

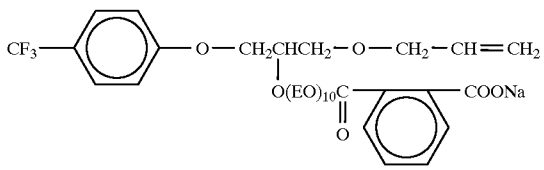

The following Examples and Tests were carried out using the following compounds of the present invention obtained in the above-mentioned Production Examples: (1-b), (5-b), (11)–(15), (17-b), (22-b) and (26). The following compounds were used, for comparison.

Comparative Compound 1

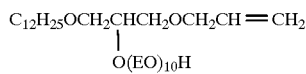

Comparative Compound 2

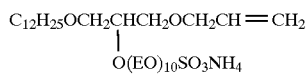

Comparative Compound 3

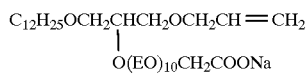

Example 1

The surfactants of the present invention (1-b), (5-b), (11)–(15), (17-b), (22-b) and (26) were tested for their carbon black dispersibility. The test method is given as follows.

Into a 100 ml stoppered measuring cylinder was added 1 g of the above-mentioned surfactant and 10 g of carbon black: they were dissolved and dispersed in water and the volume was adjusted to 100 ml. Then the measuring cylinder was shaken 100 times in one minute and susequetly allowed to stand at 25° C. for 1 hour. Then 30 cc of the liquid was taken from the liquid's surface and filtered through a glass filter, dried at 105° C., the residue left on the glass filter was weighed and dispersibility was measured according to the following formula.

Dispersing performance (%)={the weight of the residue left on the glass filter (g)/3}×100

TABLE 1

|        | (%) |
|--------|-----|
| (1-b)  | 96  |
| (5-b)  | 92  |
| (11)   | 95  |
| (12)   | 94  |
| (13)   | 92  |
| (14)   | 95  |
| (15)   | 97  |
| (17-b) | 93  |
| (22-b) | 98  |
| (26)   | 94  |

Example 2

Emulsion polymerization of styrene, butadiene and acrylonitrile monomers was carried out using the emulsifying agent of the present invention for emulsion polymerization: (1-b), (5-b), (11)–(15), (17-b), (22-b) or (26), or the comparative compound (1)–(3). The mechanical stability of the polymer emulsion obtained and water resistance of the polymer film derived from the polymer emulsion were measured.

<Polymerization Method>

A high pressure reactor wherein the system was purged with nitrogen gas was charged with 110 g of water and 4.0 g of the emulsifying agent of the present invention for emulsion polymerization: (1-b), (5-b), (11)–(15), (17-b), (22-b) or (26), or the comparative compound (1)–(3) was dissolved therein. Then 1 g of potassium persulfate was added thereto and 90 g of butadiene was fed thereto over 5 hours. Then maturation was carried out to give a polybutadiene latex.

To the polybutadiene latex obtained was added 150 g of water and 2.0 g of the emulsifying agent of the present invention for emulsion polymerization: (1-b), (5-b), (11)–(15), (17-b), (22-b) or (26), or the comparative compound (1)–(3) was dissolved therein. The system was purged with nitrogen, then 0.5 g of potassium persulfate was added to the reactor and mixed monomers comprising 40 g of styrene monomer and 10 g of acrylonitrile monomer were fed thereto over a period of 2 hours. After the feeding was completed, the mixture was matured for 4 hours to give an ABS latex resin.

Example 3

Emulsion polymerization of ethyl acrylate monomer was carried out using the emulsifying agent of the present invention for emulsion polymerization: (1-b), (5-b), (11)–(15), (17-b), (22-b) or (26), or the comparative compound (1)–(3). The mechanical stability and the foaming property of the obtained polymer emulsion and the water resistance of the polymer film obtained from the polymer emulsion were measured.

<Polymerization Method>

A reactor equipped with a reflux condenser, a stirrer, a dropping funnel and a thermometer was charged with 120 g of water and the system was purged with nitrogen. 4 g of the emulsifying agent of the present invention for emulsion polymerization: (1-b), (5-b), (11)–(15), (17-b), (22-b) or (26), or the comparative compound (1)–(3) was dissolved in 80 g of methyl acrylate and 8.4 g of the resulting solution, 0.08 g of potassium persulfate and 0.04 g of sodium hydrogen sulfite were added to the reactor and polymerization was started at 50° C. The remaining monomer and the emulsifying agent for emulsion polymerization were continuously added to the reactor dropwise over 2 hours and after the dropping was completed, the mixture was matured for 2 hours to give an emulsion.

The resins obtained in the above-mentioned Examples 2 and 3 were examined according to the following test methods.

<Test Method>

Mechanical Stability 50 g of the emulsion was rotated by a Mallon Stability Tester under the following conditions: 10 kg and 1000 rpm for 5 minutes. The resulting aggregate was filtered through a metal net of 100 mesh and the residue was washed with water, dried at 105° C. for 2 hours, and the weight was shown in terms of percent by weight based on the solid content.

Acid Deposition Test 10 ml of 1N hydrochloric acid was added to 100 g of the ABS emulsion and the mixture was stirred at 50° C. for 5 minutes and allowed to stand. Then the aggregation of ABS resin was observed.

⊚: The resin was aggregated completely and the supernatant became transparent.

○: A part of the resin was aggregated and the supernatant was milky white.

X: No aggregation was observed.

Water resistance of the film

The water resistance of the film was measured by the time required for the polymer film having a thickness of 0.2 mm to be whitened by the water immersion method, and evaluated according to the following criteria:

⊚: one day or more,

○: one hour or more, and

X: less than one hour.

TABLE 2

|  | mechanical stability (%) | acid deposition |
| --- | --- | --- |
| present invention |  |  |
| (1-b) | 12.3 | ⊚ |
| (5-b) | 13.4 | ⊚ |
| (11) | 11.6 | ⊚ |
| (12) | 14.8 | ⊚ |
| (13) | 13.2 | ⊚ |
| (14) | 14.4 | ⊚ |
| (15) | 15.5 | ⊚ |
| (17-b) | 13.1 | ⊚ |
| (22-b) | 14.9 | ⊚ |
| (26) | 14.1 | ⊚ |
| comparative |  |  |
| (1) | 24.1 | x |
| (2) | 20.5 | x |
| (3) | 21.3 | x |

TABLE 3

|  | mechanical stability (%) | water resistance |
| --- | --- | --- |
| present invention |  |  |
| (1-b) | 11.5 | ⊚ |
| (5-b) | 12.8 | ⊚ |
| (11) | 11.9 | ⊚ |
| (12) | 13.1 | ⊚ |
| (13) | 14.9 | ⊚ |
| (14) | 13.3 | ⊚ |
| (15) | 11.5 | ⊚ |
| (17-b) | 12.8 | ⊚ |
| (22-b) | 15.5 | ⊚ |
| (26) | 16.1 | ⊚ |
| comparative |  |  |
| (1) | 25.3 | x |
| (2) | 24.9 | x |
| (3) | 21.7 | x |

Example 4

A glass-lined autoclave was charged with 150 g of deionized water, 2 g of the dispersing agent of the present invention for suspension polymerization: (1-b), (5-b), (11)–(15), (17-b), (22-b) or (26), or the comparative compound (1)–(3), as well as 0.2 g of di-2-ethylhexyl peroxy carbonate, then the autoclave was deaerated to 50 mmHg to remove oxygen, and 100 g of vinyl chloride monomer was added thereto and heated to 57° C. while stirring at 500 rpm to carry out polymerization. The pressure in the autoclave was 8.0 kg/cm$^2$G when the polymerization was started, but 7 hours after the start of the polymerization, it became 4.0 kg/cm$^2$G; then the polymerization was stopped and the unreacted vinyl chloride monomer was purged, and the contents were taken out and dehydrated and dried. The thus obtained resins were examined by the following test methods.

Particle Size Distribution

The particle size distribution was analyzed by dry sieving analysis using a Tyler Mesh Standard metal mesh.

Water Resistance

A film of vinyl chloride resin having a thickness of 0.5 mm was formed and immersed in warm water at 50° C.; the time required for the film to be whitened was measured.

TABLE 4

|  | particle size distribution | water resistance |
|---|---|---|
| present invention | | |
| (1-b) | 0 | ◎ |
| (5-b) | 0 | ◎ |
| (11) | 0 | ◎ |
| (12) | 0 | ◎ |
| (13) | 0 | ◎ |
| (14) | 0 | ◎ |
| (15) | 0 | ◎ |
| (17-b) | 0 | ◎ |
| (22-b) | 0 | ◎ |
| (26) | 0 | ◎ |
| comparative | | |
| (1) | 12 wt % | x |
| (2) | 11 wt % | x |
| (3) | 15 wt % | x |

Example 5

A reactor equipped with a reflux condenser, a stirrer, a dropping funnel and a thermometer was charged with 100 g of xylene and the system was purged with nitrogen. Separately, a mixed solution comprising of 150 g of styrene, 7.5 g of the resin reforming agent of the present invention: (1-b), (5-b), (11)–(15), (17-b), (22-b), or (26), or the comparative compound (1)–(3), 2 g of benzoyl peroxide, and 1 g of di-tertiary butyl peroxide was prepared and continuously added to the reactor dropwise at a reaction temperature of 130° C. over a period of 2 hours. Furthermore, a mixed solution of 10 g of xylene, 0.5 g of benzoyl peroxide, and 0.5 g of di-tertiary butyl peroxide was added thereto dropwise and subjected to reaction for 2 hours, cooled, and then 90 g of xylene was added thereto to provide a polymer solution.

Example 6

A reactor equipped with a reflux condenser, a stirrer, a dropping funnel and a thermometer was charged with 100 g of xylene and the system was purged with nitrogen. Separately, a mixed solution comprising 150 g of butyl acrylate, 5 g of methacrylic acid, 15 g of the resin reforming agent of the present invention: (1-b), (5-b), (11)–(15), (17-b), (22-b) or (26), or the comparative compound (1)–(3), 2 g of benzoyl peroxide, and 0.5 g of di-tertiary butyl peroxide was prepared and it was continuously added to the reactor dropwise at a reaction temperature of 130° C. over a period of 2 hours. Furthermore, a mixed solution of 10 g of xylene, 0.5 g of benzoyl peroxide, and 0.5 g of di-tertiary butyl peroxide was added thereto dropwise and subjected to reaction for 2 hours, cooled, and then 90 g of xylene was added to provide a polymer solution.

A polymer film having a thickness of 0.2 mm was produced from the polymer solution obtained in the above-mentioned Example 5 and Example 6 according to a conventional method, and anti-fogging properties and anti-static properties were evaluated by the following methods respectively.

<Evaluation Method>

Anti-fogging Properties of the Film

The contact angle of water to the above-mentioned polymer film was measured.

Surface Resistivity of the Film (anti-static properties)

The above-mentioned polymer film was allowed to stand in an atmosphere of 50% humidity and 20° C. temperature for 24 hours; then surface resistivity was measured. Then, the polymer film was washed with a household kitchen detergent and rinsed with ion exchanged water thoroughly and the moisture on the surface was dried. The film was allowed to stand in an atmosphere of 50% humidity and 20° C. temperature for 24 hours; then surface resistivity was measured.

TABLE 5

|  | contact angle(°) | surface registvity ($\Omega$) | |
|---|---|---|---|
|  |  | prior to water treatment | after water treatment |
| present invention | | | |
| (1-b) | 31.3 | $2.7 \times 10^{10}$ | $2.6 \times 10^{12}$ |
| (5-b) | 31.2 | $2.6 \times 10^{10}$ | $2.4 \times 10^{12}$ |
| (11) | 31.1 | $1.8 \times 10^{10}$ | $1.4 \times 10^{12}$ |
| (12) | 32.4 | $1.5 \times 10^{10}$ | $1.9 \times 10^{12}$ |
| (13) | 31.7 | $2.3 \times 10^{10}$ | $2.1 \times 10^{12}$ |
| (14) | 32.5 | $3.3 \times 10^{10}$ | $2.9 \times 10^{12}$ |
| (15) | 32.1 | $2.4 \times 10^{10}$ | $2.1 \times 10^{12}$ |
| (17-b) | 32.6 | $3.6 \times 10^{10}$ | $3.1 \times 10^{12}$ |
| (22-b) | 31.8 | $1.9 \times 10^{10}$ | $2.7 \times 10^{12}$ |
| (26) | 32.3 | $3.3 \times 10^{10}$ | $1.9 \times 10^{12}$ |
| comparative | | | |
| (1) | 53.2 | $4.8 \times 10^{11}$ | $3.9 \times 10^{13}$ |
| (2) | 52.4 | $4.2 \times 10^{11}$ | $4.1 \times 10^{13}$ |
| (3) | 51.6 | $4.5 \times 10^{11}$ | $2.2 \times 10^{13}$ |

TABLE 6

|  | contact angle(°) | surface registvity ($\Omega$) | |
|---|---|---|---|
|  |  | prior to water treatment | after water treatment |
| present invention | | | |
| (1-b) | 31.3 | $1.3 \times 10^{10}$ | $2.7 \times 10^{12}$ |
| (5-b) | 31.8 | $2.4 \times 10^{10}$ | $6.1 \times 10^{12}$ |
| (11) | 31.2 | $2.4 \times 10^{10}$ | $3.5 \times 10^{12}$ |
| (12) | 32.7 | $3.5 \times 10^{10}$ | $4.2 \times 10^{12}$ |
| (13) | 31.1 | $3.6 \times 10^{10}$ | $3.6 \times 10^{12}$ |
| (14) | 32.5 | $2.2 \times 10^{10}$ | $6.1 \times 10^{12}$ |
| (15) | 32.4 | $2.9 \times 10^{10}$ | $8.1 \times 10^{12}$ |
| (17-b) | 31.6 | $2.8 \times 10^{10}$ | $4.3 \times 10^{12}$ |
| (22-b) | 31.2 | $3.1 \times 10^{10}$ | $9.9 \times 10^{12}$ |
| (26) | 31.3 | $6.1 \times 10^{10}$ | $5.2 \times 10^{12}$ |
| comparative | | | |
| (1) | 51.8 | $1.9 \times 10^{11}$ | $2.6 \times 10^{13}$ |
| (2) | 50.9 | $2.6 \times 10^{11}$ | $5.9 \times 10^{13}$ |
| (3) | 51.6 | $6.8 \times 10^{11}$ | $7.3 \times 10^{13}$ |

Example 7

A kneader was charged with 100 g of polypropylene resin pellets and 5 g of the resin reforming agent of the present invention: (1-b), (5-b), (11)–(15), (17-b), (22-b) or (26), or the comparative compound (1)–(3) and kneaded at 210° C. for 30 minutes. Then the resin was cast into a mold of 10 cm×10 cm×5 cm to prepare a test piece.

Example 8

A kneader was charged with 100 g of polystyrene resin pellets and 5 g of the resin reforming agent of the present invention (1-b), (5-b), (11)–(15), (17-b), (22-b) or (26), or the comparative compound (1)–(3) and kneaded at 210° C. for 30 minutes. Then the resin was cast into a mold of 10 cm×10 cm×5 cm to prepare a test piece.

The test pieces obtained were used to measure the antifogging properties and the surface resistivity in a way analogous to that used in Example 5 and Example 6.

TABLE 7

|  | contact angle (°) | surface resistivity (Ω) | |
|---|---|---|---|
|  |  | prior to water treatment | after water treatment |
| present invention |  |  |  |
| (1-b) | 35.5 | $4.7 \times 10^{10}$ | $3.8 \times 10^{13}$ |
| (5-b) | 38.4 | $5.6 \times 10^{10}$ | $4.6 \times 10^{13}$ |
| (11) | 40.3 | $6.3 \times 10^{10}$ | $3.2 \times 10^{13}$ |
| (12) | 36.6 | $5.6 \times 10^{10}$ | $2.9 \times 10^{13}$ |
| (13) | 35.1 | $7.7 \times 10^{10}$ | $8.1 \times 10^{13}$ |
| (14) | 39.1 | $4.9 \times 10^{10}$ | $6.2 \times 10^{13}$ |
| (15) | 37.2 | $6.3 \times 10^{10}$ | $7.5 \times 10^{13}$ |
| (17-b) | 36.6 | $4.8 \times 10^{10}$ | $3.6 \times 10^{13}$ |
| (22-b) | 37.3 | $5.2 \times 10^{10}$ | $4.9 \times 10^{13}$ |
| (26) | 35.5 | $5.9 \times 10^{10}$ | $3.1 \times 10^{13}$ |
| comparative |  |  |  |
| (1) | 56.9 | $9.9 \times 10^{11}$ | $8.7 \times 10^{14}$ |
| (2) | 55.3 | $1.2 \times 10^{12}$ | $8.5 \times 10^{14}$ |
| (3) | 58.4 | $7.5 \times 10^{11}$ | $1.1 \times 10^{15}$ |

TABLE 8

|  | contact angle (°) | surface resistivity (Ω) | |
|---|---|---|---|
|  |  | prior to water treatment | after water treatment |
| present invention |  |  |  |
| (1-b) | 35.2 | $6.1 \times 10^{10}$ | $4.2 \times 10^{13}$ |
| (5-b) | 38.3 | $5.4 \times 10^{10}$ | $3.4 \times 10^{13}$ |
| (11) | 36.6 | $2.4 \times 10^{10}$ | $7.0 \times 10^{13}$ |
| (12) | 35.1 | $4.5 \times 10^{10}$ | $2.9 \times 10^{13}$ |
| (13) | 37.3 | $8.3 \times 10^{10}$ | $3.8 \times 10^{13}$ |
| (14) | 36.4 | $6.2 \times 10^{10}$ | $5.1 \times 10^{13}$ |
| (15) | 39.6 | $4.3 \times 10^{10}$ | $5.0 \times 10^{13}$ |
| (17-b) | 38.5 | $3.6 \times 10^{10}$ | $6.3 \times 10^{13}$ |
| (22-b) | 35.4 | $9.3 \times 10^{10}$ | $2.2 \times 10^{13}$ |
| (26) | 36.3 | $7.1 \times 10^{10}$ | $4.3 \times 10^{13}$ |
| comparative |  |  |  |
| (1) | 57.6 | $8.8 \times 10^{11}$ | $5.4 \times 10^{14}$ |
| (2) | 58.1 | $7.5 \times 10^{11}$ | $7.4 \times 10^{14}$ |
| (3) | 55.5 | $8.3 \times 10^{11}$ | $9.1 \times 10^{14}$ |

Example 9

The following tests 1–4 were carried out on the above-mentioned stain-proofing agent of the present invention: (1-b), (5-b), (11)–(15), (17-b), (22-b) or (26), or the comparative compound (1)–(3). Monochlorobenzene in an amount of 0.6%, benzyl peroxide as a polymerization initiator in an amount of 0.1% and water as a solvent were mixed to provide an emulsion and the stain-proofing agent of the present invention or the comparative compound was added in an amount of 2% to provide a polymerization solution. A pressure resisting type stainless pot was charged with polyester cloth (5 sheets of 5×5 cm, 0.15 g) and 1 liter of the polymerization solution, then hermetically sealed, and heated while stirring in an oil bath at 110° C. for 2 hours to carry out graft polymerization of the polyester cloth to obtain a cloth made of stainproof polyester fibers.

The antifouling properties of the polyester cloth thus obtained and those of untreated polyester cloth were evaluated as follows.

(a) Sample

One of the 5 pieces of polyester cloth was used as a standard test piece for judging soil removing properties and soil redeposition prevention properties; two pieces were used as samples for the soil removing test. The remaining two pieces were used as samples for the soil redeposition prevention property test.

(b) Soil Removing Property

Soiling liquid: 1.0 g of carbon black, 1.0 g of beef tallow, 5.0 g of liquid paraffin and 1,000 cc of carbon tetrachloride were mixed and used.

0.3 ml of the soiling liquid was dropped onto two sample pieces and they were allowed to stand for 24 hours, then washed according to (d-1). The condition of the stain left after the washing was judged by the color fastness gray scale defined by JIS L-0805 and classified into 5 classes; (5: good–1: bad) (washed only once). The above-mentioned cycle comprising dropping the soiling liquid, drying, washing and drying was repeated 19 times and the condition of the stain remaining was judged in a similar manner (washed 20 times).

(c) Soil Redeposition Preventing Properties

Soil redeposition liquid: 20 g of the soiling liquid used in (b) and 10 g of a nonionic surfactant were diluted with tap water to 10 liters, and used.

Two sample pieces were put into the soil redeposition liquid, stirred at a bath ratio of 1:50 and at a temperature of 90° C. for 10 minutes. Then the sample pieces were according to (d-2), and dried. Then the condition of the stain left after the washing was judged by the color fastness gray scale defined by JIS L-0805 and classified into 5 classes, (5: good–1: bad) (washed only once). The above-mentioned cycle comprising immersing with the soil redeposition liquid, washing and drying was further repeated 19 times and the condition of the stain remaining was judged in a similar manner (washed 20 times).

(d) Washing Conditions (d-1): The washing conditions were set in similitude of an ordinary house. That is, a home use washing machine (2.2 kg) was used and household synthetic powder detergent was added in an amount of 40 g/30 l. Washing was carried out for 5 minutes with the water temperature of 40° C. Then rinsing was carried out at normal temperature without running water for 5 minutes.

(d-2): A home-use washing machine (2.2 kg) was used and rinsing at normal temperature without running water was carried twice out for 5 minutes.

TABLE 9

|  | wash cycle | stainproof property (class) | |
|---|---|---|---|
|  |  | soil removing | soil redeposition prevention |
| present invention |  |  |  |
| (1-b) | 1 | 5 | 5 |
|  | 20 | 4 | 4 |
| (5-b) | 1 | 5 | 4.5 |
|  | 20 | 4.5 | 4 |
| (11) | 1 | 4.5 | 4.5 |
|  | 20 | 4 | 4 |
| (12) | 1 | 5 | 5 |
|  | 20 | 4.5 | 4.5 |
| (13) | 1 | 5 | 4.5 |

TABLE 9-continued

| | | stainproof property (class) | |
|---|---|---|---|
| | wash cycle | soil removing | soil redeposition prevention |
| | 20 | 4 | 3.5 |
| (14) | 1 | 5 | 4.5 |
| | 20 | 4.5 | 4 |
| (15) | 1 | 4.5 | 5 |
| | 20 | 4 | 4.5 |
| (17-b) | 1 | 5 | 4.5 |
| | 20 | 4 | 4 |
| (22-b) | 1 | 4.5 | 4.5 |
| | 20 | 4 | 4 |
| (26) | 1 | 4 | 5 |
| | 20 | 4 | 4 |
| comparative | | | |
| (1) | 1 | 2 | 2 |
| | 20 | 1.5 | 2 |
| (2) | 1 | 2 | 2 |
| | 20 | 2 | 2 |
| (3) | 1 | 2 | 2 |
| | 20 | 1.5 | 2 |
| None | 1 | 1.5 | 2 |
| | 20 | 1.5 | 2 |

INDUSTRIAL APPLICABILITY

By use of the compound of the present invention as an emulsifying agent for emulsion polymerization or as a dispersing agent for suspension polymerization, the resin obtained by the emulsion polymerization or the suspension polymerization will not show lowered water resistance, weather resistance or durability. When used as a resin reforming agent, the compound of the present invention can impart various physical properties to the resin. When used as a soil resistant finish for polyester fibers, the compound of the present invention can impart antifouling properties to the polyester fiber.

We claim:

1. A compound represented by the general formula (1):

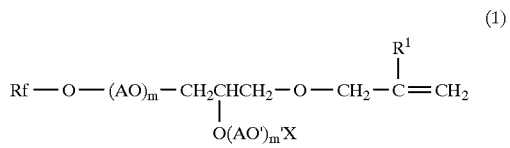

(1)

wherein, $R^1$ represents a hydrogen atom or a methyl group, Rf represents a hydrocarbon group in which one or more hydrogen atoms are replaced by a fluorine atom or atoms, or an acyl group in which one or more hydrogen atoms are replaced by a fluorine atom or atoms, AO and AO' represent a group selected from an oxyalkylene group having 2–4 carbon atoms or a styrene oxide residue, m is 0 or a number between 1 and 1,000, m' is a number between 1 and 1,000, and X represents a hydrogen atom or a hydrophilic group.

2. A compound according to claim 1, wherein X in the formula (1) is a hydrophilic group represented by —$SO_3M$, —$R^2$—COOM, —$PO_3M_2$, —$PO_3MH$ or —CO—$R^3$—COOM (wherein M represents a hydrogen atom, an alkali metal atom, alkaline earth metal atom, ammonium, ammonium of an alkylamine or ammonium of an alkanolamine (provided that the alkaline earth metal atom is ½), $R^2$ represents an alkylene group, and $R^3$ represents a residue of a dibasic acid or an anhydride thereof).

3. A compound according to claim 1, wherein Rf is a group represented by $F(CF_2)_{n-1}CH_2$—, $H(CF_2)_{n'-1}CH_2$— (provided that n is a number not less than 1, and n' is a number not less than 2), or a perfluoroacyl group.

4. A surfactant comprising a compound according to claim 1.

5. An emulsifying agent for emulsion polymerization comprising a compound according to claim 1.

6. A dispersing agent for suspension polymerization comprising a compound according to claim 1.

7. A resin reforming agent comprising a compound according to claim 1.

8. A stain-proofing agent for polyester fibers comprising a compound according to claim 1.

9. A compound represented by the general formula (1):

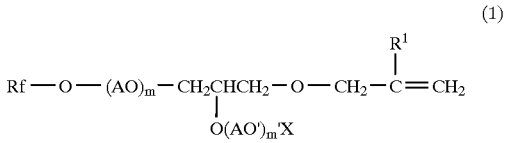

(1)

wherein, $R^1$ represents a hydrogen atom or a methyl group, Rf represents a hydrocarbon group in which one or more hydrogen atoms are replaced by a fluorine atom or atoms, or an acyl group in which one or more hydrogen atoms are replaced by a fluorine atom or atoms, AO and AO' represent a group selected from an oxyalkylene group having 2–4 carbon atoms or a styrene oxide residue, m and m' are 0 or a number between 1 and 1,000, and X represents a hydrophilic group represented by —$SO_3M$, —$R^2$—COOM, —$PO_3M_2$, —$PO_3MH$ or —CO—$R^3$—COOM wherein M represents a hydrogen atom, an alkali metal atom, alkaline earth metal atom, ammonium, ammonium of an alkylamine or ammonium of an alkanolamine, provided that the alkaline earth metal atom is ½, $R^2$ represents an alkylene group, and $R^3$ represents a residue of a dibasic acid or an anhydride thereof.

10. A compound according to claim 9, wherein Rf is a group represented by $F(CF_2)_{n-1}CH_2$—, $H(CF_2)_{n-1}CH_2$—, provided that n is a number not less than 1, and n' is a number not less than 2, or a perfluoroacyl group.

11. A surfactant comprising a compound according to claim 9.

12. An emulsifying agent for emulsion polymerization comprising a compound according to claim 9.

13. A dispersing agent for suspension polymerization comprising a compound according to claim 9.

14. A resin reforming agent comprising a compound according to claim 9.

15. A stain-proofing agent for polyester fibers comprising a compound according to claim 9.

* * * * *